Figure 1:
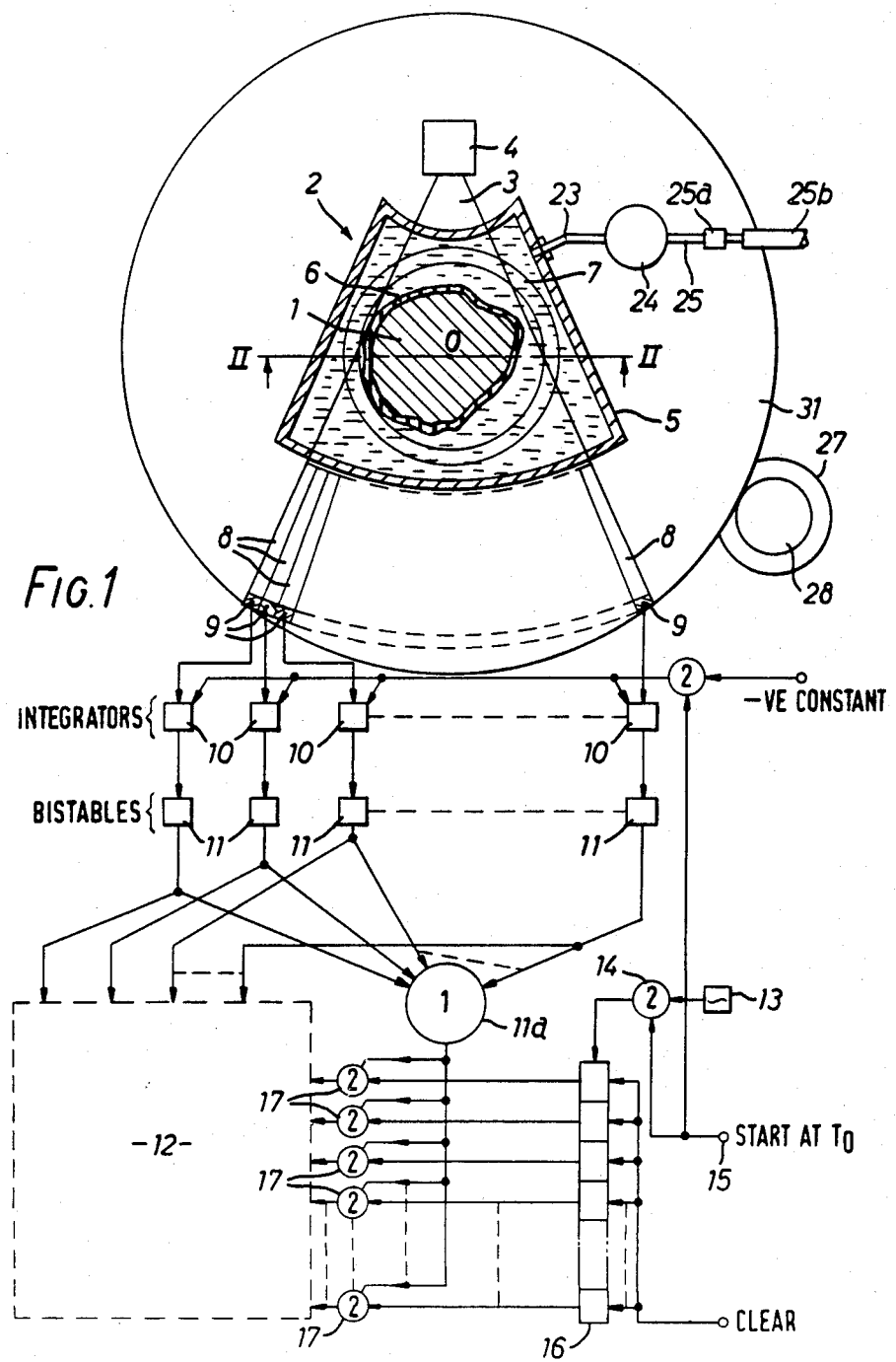

United States Patent [19]

Hounsfield

[11] Patent Number: 4,497,061
[45] Date of Patent: Jan. 29, 1985

[54] METHOD AND APPARATUS FOR RADIOGRAPHY COMPRISING CALIBRATING MEANS

[75] Inventor: Godfrey N. Hounsfield, Newark, England

[73] Assignee: EMI Limited, Hayes, England

[21] Appl. No.: 869,711

[22] Filed: Jan. 16, 1978

Related U.S. Application Data

[60] Continuation of Ser. No. 758,147, Jan. 10, 1977, abandoned, which is a division of Ser. No. 481,443, Jun. 21, 1974, Pat. No. 4,035,647, which is a division of Ser. No. 358,890, May 10, 1973, Pat. No. 3,881,110.

[30] Foreign Application Priority Data

May 17, 1972 [GB] United Kingdom ............... 23064/72

[51] Int. Cl.³ .......................... A61B 6/00; A61B 6/02; G01N 23/02
[52] U.S. Cl. ......................................... 378/18; 378/5; 378/207; 378/901; 364/414
[58] Field of Search ....................... 378/18, 207, 4, 10, 378/14, 901, 5; 364/414

[56] References Cited

U.S. PATENT DOCUMENTS

| | | | |
|---|---|---|---|
| 2,399,650 | 5/1946 | Moyer | 378/207 |
| 4,028,554 | 6/1977 | Hounsfield | 378/901 |
| 4,044,260 | 8/1977 | Hounsfield | 378/901 |
| 4,118,628 | 10/1978 | Hounsfield | 364/414 |

FOREIGN PATENT DOCUMENTS 887891 12/1971 Canada .

Primary Examiner—Alfred E. Smith
Assistant Examiner—T. N. Grigsby
Attorney, Agent, or Firm—Cooper, Dunham, Clark, Griffin & Moran

[57] ABSTRACT

Apparatus for investigating a part of a body intermediate the extremities thereof by means of X- or γ-radiation is disclosed. The body part is surrounded by a liquid medium; the liquid medium being retained in an enclosure having a tubular inner wall formed of flexible material, and the body part is located within the inner wall. The liquid medium can be pressurized to cause the flexible inner wall to fit intimately the periphery of the body part.

11 Claims, 6 Drawing Figures

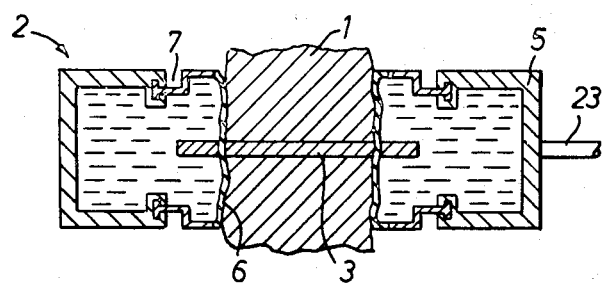
FIG. 2
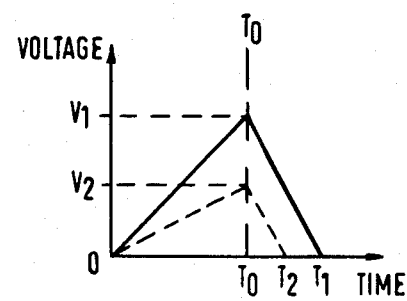
FIG. 3
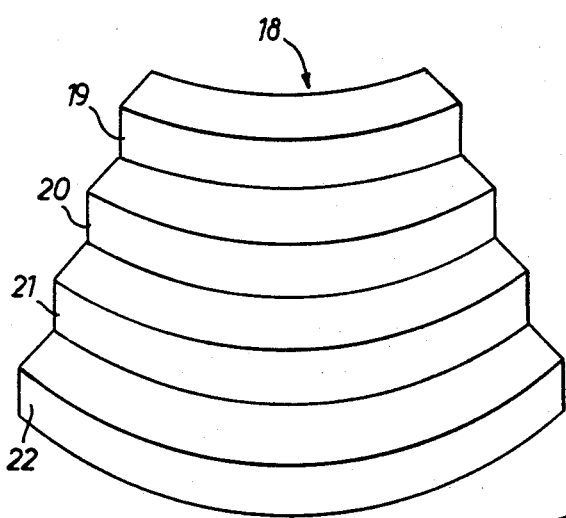
FIG. 4a
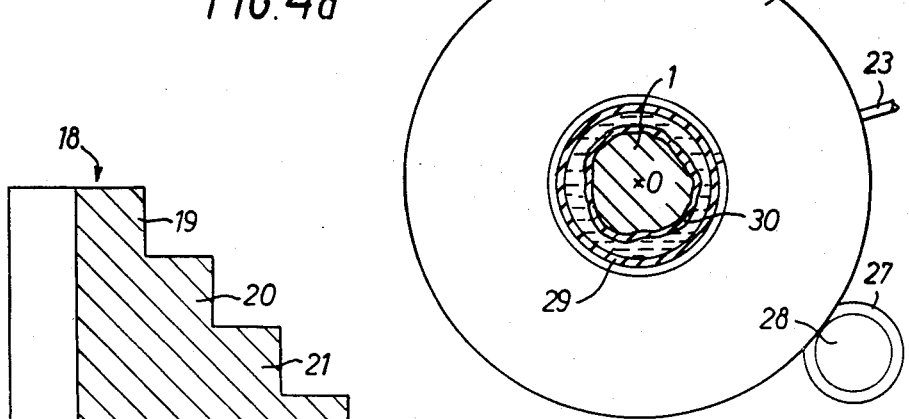
FIG. 4b
FIG. 5

"4,497,061"

METHOD AND APPARATUS FOR RADIOGRAPHY COMPRISING CALIBRATING MEANS

This is a continuation of application Ser. No. 758,147 filed on Jan. 10, 1977 and now abandoned, which in turn is a divisional application of Ser. No. 481,443, filed on June 21, 1974 and now U.S. Pat. No. 4,035,647, which in turn is a divisional application of Ser. No. 358,890, filed on May 10, 1973 and now U.S. Pat. No. 3,881,110.

The present invention relates to radiography and it relates especially to techniques for obtaining information indicative of the presence or absence of anomalies in the interior of a body, despite the presence of other material in the body.

In the Specification of U.S. Patent Application Ser. No. 212,778 now U.S. Pat. No. 3,778,614 there is described and claimed a method of, and apparatus for, examining a body by means of radiation such as X- or γ-radiation. The use of the method or apparatus permits the calculation of the transmission or absorption coefficients of substantially all elements in an at least two dimensional, notional matrix of elements defined in the body being examined. This is achieved by causing radiation to pass through the body along a plurality of discrete paths of cross-sectional dimensions similar to those of said elements, said paths being oriented to pass through respective combinations of the elements in said notional matrix. The overall absorption of radiation along each of the discrete paths is detected and sufficient paths are used to enable the calculation of the absorption or transmission coefficients of substantially all elements in said notional matrix.

The present invention is concerned with a similar arrangement, but has the aim of providing means for locating an elongated member, such as the human torso, relative to the source of radiation and the detectors.

According to the invention there is provided radiographic apparatus for examining part of a body by means of penetrating radiation, such as X- or γ-radiation, including a source of said radiation disposed at one side of said body part, detector means, disposed at the side of said body part remote from the source, for detecting said radiation after it has passed through said body part, means for orbiting the source and the detector means around an axis in said body part so as to expose said body part to said radiation from a plurality of different directions, and locating means for locating said body part relative to the source and the detector means, said locating means including an enclosure for a liquid medium arranged to surround said body, said enclosure having outer and inner walls; said inner wall comprising a substantially tubular, flexible member having open ends whereby a body part intermediate the extremities of said body can be examined.

In order that the invention may be clearly understood and readily carried into effect, the same will now be described, by way of example only, with reference to the accompanying drawings, of which:

FIG. 1 illustrates, partly in a plan section and partly in block schematic form, apparatus in accordance with one example of the invention, FIG. 2 shows a section on lines II—II of FIG. 1, FIG. 3 illustrates waveforms explanatory of the operation of the apparatus shown in FIG. 1, FIGS. 4(a) and 4(b) show, in perspective view and cross-sectional form respectively, a calibration device suitable for use with the apparatus shown in FIG. 1, and FIG. 5 shows an alternative form of the invention.

Referring now to the drawings, and more particularly to FIGS. 1 and 2, a body 1 to be investigated is mounted in an arrangement shown generally at 2 so that is can be illuminated by a fan-shaped sweep 3 of penetrative radiation, such as X- or γ-radiation, derived from a source 4.

The arrangement 2, in this example, comprises an enclosure of which the outer walls 5 are formed of the material known by the Registered Trade Mark "Perspex" or another suitable material. The arrangement is provided with a central aperture in which the body 1 is situated, the aperture being surrounded by a tubular, flexible wall 6 formed, for example, of rubber. The enclosure between the walls 5, 6 is filled with water as indicated by the horizontal shading lines. Water can be pumped into or out of said enclosure by means of a pump 24 which is reversible in its operation and which communicates with said enclosure by means of a pipe 23 and with a water reservoir (not shown) via a pipe 25, a closure valve 25a and a removeable pipe 25b. Water is pumped out of said enclosure to allow the tubular wall 6 to expand outwardly so that the body 1 can be inserted therein and then water is pumped into said enclosure to cause the wall 6 to fit snugly around the part of body 1 which is to be investigated. In order that the body 1 and the flexible wall 6 may remain stationary whilst the remainder of the enclosure is rotated, a rotary water seal 7 is provided in the arrangement 2. The fan shaped sweep 3 passes through the arrangment 2 as shown in FIG. 2 and it will be appreciated that the snug fit between the flexible wall 6 and the body 1 must be maintained at least over the area through which the beam passes.

Having passed through the body 1, the fan shaped sweep 3 is incident upon a plurality of radially extending collimators 8 and the field of view of each collimator defines a respective, discrete path of radiation through the body 1. In one example, 160 such collimators are used. In order that the overall degree of absorption of radiation along each discrete path can be monitored, each collimator 8 communicates with a respective radiation detector 9 which may take one of several forms to be described hereinafter.

Each detector 9 feeds a respective integrator circuit 10 and the arrangement is such that (referring to FIG. 3) each integrator receives signals from its respective radiation detector for a given exposure period $T_o$. At time $T_o$, a negative voltage is applied in parallel to all the integrators 10 causing them each to discharge towards zero potential. The time taken for the charge held in a given integrator to reach zero potential will clearly be determined by the amount of charge accumulated up to $T_o$, thus if, for example a first detector accumulated charge corresponding to a potential $V_1$ and a second detector accumulated a lesser amount of charge corresponding to a potential $V_2$, the integrator associated with the first detector would reach zero potential in time $(T_1-T_o)$ whereas the integrator associated with the second detector would reach zero potential in the lesser time $(T_2-T_o)$. Accordingly, referring again to FIG. 1, each integrator 10 is arranged to feed a respective bistable circuit 11 which is such that it provides an output pulse when the input signal thereto reaches zero potential from a more positive potential. The output pulses from all the circuits 11 pass on the one hand through a common OR gate 11a, and on the other hand as path identity signals to a store 12 associated with a computer (not shown).

An oscillator 13 is arranged to generate regularly occurring pulses at a rapid rate and these are applied to an AND gate 14. The gate 14 is enabled at time $T_o$ by the same control signal as was used to apply the negative potential to the integrator 10, the control signal being applied to a terminal 15, and is arranged to pass the pulses generated by oscillator 13 to a counter 16 continuously from the time $T_o$ to the time when the last of the integrators indicates zero potential.

The counter 16 is a multistage binary counter having sufficient capacity for counting the number of pulses which would be generated by oscillator 13 during the period from $T_o$ to the maximum possible time taken for one of the integrators 10 to indicate zero potential i.e., in the case of zero absorption of the radiation along a given path.

Each stage of counter 16 is connected, via a respective AND gate 17, as a decay time input to the store 12 and the gates 17 are all simultaneously enabled when a pulse derived from any one (or more) of the bistable circuits 11 passes through the OR gate 11a. The store 12 thus receives both path identity and decay time information and the computer is arranged to correlate this information to provide a figure representing the absorption (or transmission) of said radiation along each path. These figures are then converted into logarithmic values and processed, for example in the manner described in the aforementioned Patent Specification, to provide a representation or a visual record or display of the absorption (or transmission) coefficients of substantially all the elements in a two-dimensional notional matrix of elements defined in the body 1.

In this example, the fan shaped sweep is substantially planar, but it could alternatively be caused to have a greater thickness dimension so as to permit a three dimensional notional matrix of elements defined in the body 1 to be investigated.

In operation, the source 4, the part of arrangement 2 outside the water seal 7, together with the pump 24, pipes 23 and 25 and the valve 25a, from which pipe 25b is then detached, the collimators 8 and the detectors 9 are orbited, about the center O of the arrangement 2, relative to the body 1 in order to expose the body 1 to radiation from a plurality of different directions. For this purpose the aforementioned components are mounted on a turntable 26 which has an aperture therein corresponding to the diameter of the water seal 7, the turntable being driven by means of an electric motor 27 via a suitable drive mechanism 28 which may comprise, for example, a toothed gear wheel adapted to co-operate with gear teeth provided around the periphery of the turntable 16. It is preferable in some circumstances, especially when the human torso is examined, that the aforementioned components be rotated at a rapid rate in order that the irradiation of the torso can be completed sufficiently rapidly that the time available for movement of internal organs of the body (which movement could cause degradation of the resolution of the apparatus) is limited. In these circumstances, it is preferable for the aforementioned components to be rotated continuously rather than step-wise (as described in the aforementioned Patent Specification). Because of this continuous rotation, each exposure time effectively corresponds to the time taken for the aforementioned components to rotate through a small angle, and in order to reduce or avoid confusion of detail produced by the relative movement between the source and detectors and the body, the computer can be programmed to take account of this.

To evaluate zero for each detector 9 during operation of the apparatus, a shutter (not shown) may be provided between the source 4 and the arrangement 2. This shutter is rotated so that it intermittently interrupts the radiation during each exposure time and the zero reading obtained when the beam of radiation is interrupted is subtracted from the calculated absorption (or transmission) coefficient. The shutter drive mechanism must be synchronised with the mechanism for rotating the aforementioned components of the apparatus so as to enable a zero to be evaluated during each exposure time.

It is possible, as previously mentioned, to utilise one of several arrangements as the detectors 9 and these arrangements are set out below.

EXAMPLE 1

Silicon photodetectors together with an associated wavelength converter phosphor, such as a CsI crystal, for converting the penetrative radiation into optical radiation. The silicon photodetectors can take the form, for example, of p-n junction photodiodes, p-i-n silicon photodiodes, silicon avalanche photodiodes, silicon photofets, silicon planar junction phototransistors or silicon photo-integrated circuits, a respective detector being provided for each collimator.

A problem which arises with photodetectors of this kind is dark current and the detectors require cooling to reduce this phenomenon. If however, the temperature of the array of detectors is stabilised, a higher dark current can be tolerated since it is consistent and can be allowed for by suitably programming the computer.

EXAMPLE 2

Photoemissive diodes together with a wavelength converter phosphor. The diode could comprise, for example, respective separate photodiodes for each collimator; a similar number of diodes in a common vacuum enclosure; channel multiplier diodes; small photomultipliers or gas-filled photomultiplier photocells.

There are practical limitations on attainable sizes of photoemissive diodes, but this disadvantage can be alleviated to some extent by utilising reflecting optical systems.

EXAMPLE 3

An X- (or γ-) ray sensitive vidicon. Grazing incidence reflecting optical elements made from such metals as electroless plated titanium or aluminium have made it possible to obtain good quality X-ray images without using pinhole optics. A difficulty arises however in that an imge demagnefication of about 30:1 is required.

EXAMPLE 4

A fibre-optic vidicon fed by respective fibre optic light guides from respective wavelength converter phosphors for each collimator.

EXAMPLE 5

A Digicon tube and a wavelength converter phosphor. The Digicon is a vacuum tube containing a semitransparent photoemissive cathode of the inside of the end window, a series of accelerating and focusing electrodes and a linear array of silicon p-n junction diodes on the window at the other end. A solenoidal focus field is used to direct and focus electrons emitted from the photocathode. The diodes are reverse biassed and, when struck by electrons, the phenomenon of electron bombardment induced conductivity causes them to conduct. The conduction current is about $2 \times 10^3$ or $3 \times 10^3$ times greater than the bombarding current and thus the tube is capable of detecting single photoelectrons. For this application, the Digicon requires a fibre optic end window communicating with the photocathode and fibre optic coupling between the Digicon and respective wavelength converter crystals for each collimator.

EXAMPLE 6

Photographic film. A full size medical X-ray plate is moved mechanically beneath the body in a direction perpendicular to the plane of the fan-shaped beam 3. Thus a series of lines corresponding to the transmitted radiation would be unprinted as a number of dots at each exposure angle. After developing the lines are scanned with a microdensitometer.

In any of the above examples, it can be advantageous, in order to avoid dead spaces between adjacent detectors, to construct the collimators so that adjacent paths overlap to some extent. Alternatively, however, the gaps may be covered by arranging that, in a full 360° sweep around the body, the paths not scanned on one half revolution are scanned during the next half revolution.

It is desirable, in any of the foregoing arrangments, that the individual components of the detecting means should initially be calibrated and then re-calibrated before each new body is examined thereby. To this end, a suitable arrangement has been found to be as follows.

One of the individual components (such as for example the extreme left hand collimator 8 and detector 9 shown in FIG. 1) is calibrated comprehensively by insertion of a wedge of continuously variable thickness (and hence absorbing power) between the source 4 and the collimator 8, and the output signals fed from counter 16 to the computer are noted. Thus the computer is provided with a characteristic response curve for the detecting means. Of course the wedge could be inserted between the source 4 and all the detecting means to enable an average characteristic response curve to be calculated, if desired. Once having provided the computer with a characteristic response curve, it is only necessary, during re-calibration, to provide relatively crude information to the computer, for example an indication of the responses of the detecting means to minimum and maximum amounts of radiation would be sufficient. However in this example the responses of the detecting means under two intermediate conditions, as well as under the two extreme conditions are measured. A sectoral shaped calibration member 18, made up of four layers as shown in FIGS. 4(a) and 4(b) is used, the thinnest layer 19 being adapted to transmit substantially all radiation incident thereon, the next thicker layer 20 being adapted to absorb the radiation to some extent, the layer 21 being adapted to absorb the radiation to a greater extent and the thickest layer 22 being adapted to absorb substantially all the radiation incident thereon. In addition to, or instead of being of different thicknesses the layers may be of different materials. In operation, the calibration member 18 is lowered step-wise into the path of the fan-shaped sweep 3, so that the amount of radiation passed through each layer of member 18 is monitored by each detecting means and the output signals derived from the detecting means are processed as described with reference to FIG. 1, the process terminating in a rough re-calibration curve for each component of the detecting means being applied to the computer for comparison with the stored characteristic response curve. After the comparison has been effected, the computer has a store of calibration error information which can be used automatically to weight the signals derived from respective detecting means.

The "Perspex" wall 5 of the arrangement 2 need not be of the shape shown in FIG. 1. For example the walls through which the beam 3 passes need not be arcuate; they may be planar or shaped to provide a constant attenuation to radiation throughout the arrangement 2 when the body 1 is replaced by water. Moreover, the material used to construct these walls need not be "Perspex" for example PVC or other suitable plastics materials could be used.

In the apparatus described with reference to FIG. 1, the discharge rate of the integrators 10 is arranged to be linear, and for this reason the binary numbers fed into the store 12 from the counter 16 have to be converted into logarithmic values in order that the overall absorption suffered by radiation traversing the body along a path can be expressed as the sum of the absorptions of the elements of the matrix which are disposed along said path.

An alternative arrangement is to cause the integrators to discharge in accordance with a logarithmic law. When the charge held in an integrator has decayed to a threshold level, the corresponding bistable circuit 11 is arranged to feed a pulse via "OR" gate 11a to the 'AND' gates 17. The operation from this point is the same as that described with reference to FIG. 1 except, of course, that the logarithmic conversion has already taken place so that is is unnecessary for the members fed into store 12 from the counter 16 to be so converted.

The threshold level referred to in the last preceding paragraph can be selected to suit individual applications and if a human torso is being examined, the threshold may be made such that an absorption level giving rise to a charge, in an integrator, which decays to the threshold level in a given time t' is allocated a value of zero. Correspondingly, absorption levels giving rise to changes which decay to the threshold level in times less than t' are designated positive (since greater absorption has occurred) whereas absorption levels giving rise to changes which decay to the threshold level in times greater than t' are designated negative.

It will be appreciated that in practice it is convenient for a patient to lie supine with the required part of his torso inside the tubular, flexible wall 6. This can be achieved by arranging the apparatus with its axis of rotation horizontal and by placing suitable couches or the like on either side of the apparatus, the couches being adapted to support, respectively, the upper part and the lower part of the patient's body.

In a modification of the invention which is shown in part in FIG. 5, the rotary water seal used in the apparatus shown in FIG. 1 is dispensed with since the water enclosure is designed to remain stationary while the source and detectors orbit around it. In the apparatus shown in plan and part cross-sectional view in FIG. 5, a cylindrical outer wall 29 of "Perspex" (Registered Trade Mark) or other suitable material is formed with annular end flanges (not shown). Extending between the inner peripheries of the two annular flanges is a tubular, flexible inner wall 30 formed, for example, of rubber. The X-ray source and detectors (not shown) are mounted on a turntable member 31 which is annular and rotates around the cylindrical wall 29; the axis of rotation of the turntable being coincident with the longitudinal axis of the cylindrical wall 29. The operation of the apparatus is identical to that of FIG. 1 but since the water enclosure does not rotate, the need for the rotating water seal is avoided. Also, it is possible to provide a permanent connection between a water pump such as 24 (FIG. 1) and a water reservoir, avoiding the need for a valve such as 25*a* and a removeable pipe such as 25*b* (FIG. 1).

Although in the foregoing description reference has been made to the use of water to surround the part of the body being examined, it is stressed that the invention is not limited to the use of water. Other liquid media may be used and, in particular if the body being examined is not a human body, other liquids of different densities might be preferable to water. In general it is desirable to choose the liquid medium such that its absorption to the radiation being used is similar to the average absorption of said radiation by the body being examined.

What we claim is:

1. A method of operating an apparatus for examination of objects by means of X-radiation comprising the steps of:

generating X-radiation for propagation along a plurality of beam paths which are at different angles to each other and in a substantially planar section, sensing the radiation propagated along said beam paths, introducing into said substantially planar section successive portions of a calibration device, said successive portions having different known absorption characteristics such that the radiation propagated along said plurality of paths is successively subjected to said different absorption characteristics, measuring the amount of radiation sensed by the detectors for said different portions of the calibration device and deriving a calibration characteristic for each of the detectors from the last recited measuring, and storing indications of said calibration characteristic for use in examinations of objects with said apparatus.

2. Apparatus for carrying out examination of objects by means of X-radiation, comprising:

means for generating X-radiation for propagation along a plurality of beam paths in a substantially planar section;

a plurality of detectors for sensing the radiation propagated respectively along said beam paths;

calibrating means having different known absorption characteristics in different sections which can be successively introduced into said substantially planar section so that radiation propagated along said plurality of paths is successively subjected to said different absorption characteristics;

means for measuring the amount of radiation sensed by said plurality of detectors from said different beam paths when the radiation is subjected to said different absorption characteristics; and means for deriving a calibrating characteristic for each of said detectors from said measurement and for storing indications of said calibrating characteristic for use in subsequent examinations of said objects.

3. A method of using X-radiation for examing a slice of an object extending along a planar section through the object comprising the steps of:

generating X-radiation and detecting the X-radiation after passage thereof through a calibration member of known X-ray response characteristics along each of a number of beam paths diverging coplanarly in moving through the calibration member and impinging on respective detecting devices and deriving from each detecting device an electrical output signal determined at least in part by the amount of radiation impinging thereon along the respective beam path;

deriving and storing calibration error information for each of said detecting devices based on the electrical output signals produced for the radiation impinging on the detecting device;

generating X-radiation and detecting the X-radiation with said detecting devices after passage thereof through said object along each of a number of beam paths diverging coplanarly in moving through the object, in said slice thereof, from each of a number of locations distributed along an orbit extending at least half way around the object, each beam path from any one location impinging on a different detecting device, and deriving electrical output signals from each of the detecting devices determined at least in part by the amounts of radiation impinging thereon after passing through the object along respective ones of a number of beam paths which are at an angle to each other; and producing a picture composed of indications of the X-ray response of said object slice at each of a number of elements into which the slice is divided by a finite Cartesian matrix notionally superimposed thereon based on the last recited electrical output signal and on said calibration error information.

4. A method as in claim 3 wherein the steps of deriving and storing calibration error information for each detecting device comprises deriving said information based on electrical output signals for the X-radiation impinging on the device along at least four beam paths passing through the calibration member along lines having different X-ray response characteristics.

5. A medical diagnostic X-ray machine for examining a slice of a patient extending along a planar section through the patient comprising:

X-ray source means for generating X-radiation traveling toward the patient along said section from each of a number of locations distributed along an orbit extending at least half way around the patient and means for detecting the radiation from each of said locations after passage thereof through the patient along beam paths which extend along the section and are at many different directions and for producing output signals each determined at least in part by the amount of radiation received by the detecting means along a respective one of said beam paths, said X-radiation traveling toward the patient from each of said locations as a fan made up of a number of beam paths diverging in moving away from the location, and said detecting and producing means including means for detecting each of the beam paths of a fan and for producing a respective output signal;

a calibration member of known X-ray response characteristics and means for disposing the calibration member along said section, in place of the patient slice, and for causing the generating means to generate X-radiation from at least a subset of said locations and for causing the detecting and producing means to detect the radiation therefrom received by the detecting means after passage through the calibration member rather than through the patient along at least a subset of said beam paths and to produce respective output signals; and means for deriving calibration error information for the detecting means from the last recited output signals and for storing said calibration error information for use in automatically weighting output signals produced subsequently by the detecting and producing means for beam paths passing through the patient slice.

6. A medical diagnostic X-ray machine as in claim 5 in which the deriving and producing means comprise a number of detecting devices, each of the divergent beam paths from any one of said locations being received by a different detecting device, and in which the deriving and storing means includes means for deriving and storing calibration error information for each of said detecting devices for use in automatically weighting output signals for the X-radiation along beam paths subsequently passing through the patient and received by the respective detecting device.

7. A medical diagnostic X-ray machine as in claim 5 in which the causing means include means for causing the detecting and producing means to produce an output signal for each of at least four beam paths encountering different X-ray responses in passing through the calibration member but received by the same detecting device, and the deriving and storing means include means for deriving for each detecting device calibration error information from at least said last recited output signals for the detecting device and for storing the last recited calibration error information for each detecting device for use in automatically weighting output signals for the X-radiation along beam paths subsequently passing through the patient and received by the respective detecting device.

8. A medical diagnostic X-ray machine for examining a slice of a patient which extends along a section through the patient comprising:

X-ray source means producing a beam of X-radiation originating at each of a number of orbital locations distributed along an orbit extending at least halfway around the patient and fanning out in said section from each location into a fan of radiation passing through the patient, each fan being made up of a number of beam paths which start out from a common apex at a respective one of said locations and are angularly distributed within the fan, all of the beam paths being along said section, and means for detecting the radiation comprising detecting devices at least a number of which concurrently receive the radiation which has passed through the patient along the number of beam paths making up a fan, and means for deriving from the detecting devices which receive radiation output signals each of which corresponds to the amount of radiation received by a detecting device along a beam path;

means for disposing a calibration member at said section, in place of the patient slice, and for causing the beam paths along which each detector receives radiation to pass through at least four paths in the calibration member which have different X-ray attenuation characteristics;

means for deriving from each detector device output signals corresponding to the amount of radiation received by the detector along each of the last recited at least four beam paths and for deriving therefrom calibration error signals for said detecting device; and means for storing said calibration signals for automatic weighting of the output signals corresponding to beam paths through the patient in accordance with said calibration error signals in the course of subsequently examining a patient with said machine.

9. A medical diagnostic X-ray machine for examining a patient disposed at a patient position to build up and display a two-dimensional picture of the X-ray absorption coefficients of the elements into which a slice of the patient extending along a planar section through the patient position is divided by a finite Cartesian matrix notionally superimposed on the slice comprising:

X-ray source means producing an X-radiation beam originating at an origin orbiting through at least half an orbit around the patient position, said radiation beam fanning out from the origin into a sectoral-shaped, substantially planar swath of radiation which is substantially coplanar with the section through the patient position, and means for detecting the radiation from the origin which has passed through the patient position along said swath comprising a plurality of detecting devices which at any one time view the radiation origin along respective different beam paths in the swath and means for deriving for each of the detecting devices, as the radiation origin orbits around the patient position, electrical signals which correspond to the X-ray absorption suffered by the X-radiation from the origin in passing through the patient position to reach the detecting device along a plurality of beam paths corresponding to a respective plurality of different orbital positions of the radiation origin, all of the beam paths of said plurality of beam paths being along the section and at an angle to each other;

a calibration member of known absorbing power disposable at the patient position to locate a slice of the calibration member along said section of the patient position, and means for deriving for each of the detecting devices first electrical signals corresponding to the X-ray absorption suffered by the X-radiation from the origin in passing through the calibration member slice along at least a subset of the beam paths corresponding to the detecting device and for deriving, from said first electrical signals, calibration error signals for each detecting device and for storing said calibration error signals;

means for disposing the patient at the patient position, with the patient slice being along said section in place of the calibration member, and for deriving for each of said detecting devices second electrical signals corresponding to the X-ray absorption suffered by the X-radiation from the origin in passing through the patient slice to reach the detecting device along the corresponding plurality of beam paths and for weighting the second electrical signals in accordance with said stored calibration error signals; and means for building up and displaying said two-dimensional picture of the X-ray absorption coefficient of the patient slice elements from said weighted second electrical signals.

10. A medical diagnostic X-ray machine as in claim 9 wherein the means for deriving said calibration error signals comprise means for deriving a characteristic response curve for the detecting means and for conforming the stored calibration error signals to said characteristic response curve.

11. A medical diagnostic X-ray machine as in claim 9 wherein the means for deriving said calibration error signals comprise means for deriving at least four different electrical signals, corresponding to four different X-ray absorptions suffered by the X-radiation, for each of said detecting devices and for using said four electrical signals in deriving said calibration error signals for the respective detecting device.

* * * * *